United States Patent
Sun et al.

(10) Patent No.: US 12,410,452 B2
(45) Date of Patent: Sep. 9, 2025

(54) METHOD FOR PRODUCING LYSINE FROM MICROORGANISM AND FOR CONSTRUCTING MICROORGANISM

(71) Applicant: Tianjin Institute of Industrial Biotechnology, Chinese Academy of Sciences, Tianjin (CN)

(72) Inventors: Jibin Sun, Tianjin (CN); Jiuzhou Chen, Tianjin (CN); Ping Zheng, Tianjin (CN); Wenjuan Zhou, Tianjin (CN); Xuan Guo, Tianjin (CN); Tuo Shi, Tianjin (CN); Jiao Liu, Tianjin (CN); Yanhe Ma, Tianjin (CN)

(73) Assignee: Tianjin Institute of Industrial Biotechnology, Chinese Academy of Sciences, Tianjin (CN)

( * ) Notice: Subject to any disclaimer, the term of this patent is extended or adjusted under 35 U.S.C. 154(b) by 431 days.

(21) Appl. No.: 17/758,770

(22) PCT Filed: Jan. 13, 2021

(86) PCT No.: PCT/CN2021/071517
§ 371 (c)(1),
(2) Date: Jul. 13, 2022

(87) PCT Pub. No.: WO2021/143727
PCT Pub. Date: Jul. 22, 2021

(65) Prior Publication Data
US 2023/0242952 A1    Aug. 3, 2023

(30) Foreign Application Priority Data

Jan. 15, 2020  (CN) .......................... 202010042203.2

(51) Int. Cl.
*C12P 13/08* (2006.01)
*C07K 14/34* (2006.01)
*C12N 9/06* (2006.01)
*C12N 9/12* (2006.01)

(52) U.S. Cl.
CPC .............. *C12P 13/08* (2013.01); *C07K 14/34* (2013.01); *C12N 9/0016* (2013.01); *C12N 9/1217* (2013.01); *C12Y 104/01016* (2013.01); *C12Y 207/02004* (2013.01)

(58) Field of Classification Search
None
See application file for complete search history.

(56) References Cited

U.S. PATENT DOCUMENTS

| | | | |
|---|---|---|---|
| 6,962,989 B1* | 11/2005 | Pompejus | C07H 21/02 536/23.7 |
| 8,048,650 B2 | 11/2011 | Koo et al. | |
| 9,593,354 B2 | 3/2017 | Lee et al. | |
| 10,889,843 B2 | 1/2021 | Byun et al. | |
| 11,104,925 B2 | 8/2021 | Lee et al. | |
| 2005/0003494 A1 | 1/2005 | Zelder et al. | |
| 2007/0042474 A1* | 2/2007 | Pompejus | C12P 13/06 435/85 |
| 2009/0311758 A1* | 12/2009 | Jessberger | C12P 13/04 435/106 |
| 2012/0208245 A1 | 8/2012 | Rah et al. | |
| 2014/0377816 A1 | 12/2014 | Rah et al. | |
| 2015/0337346 A1* | 11/2015 | Yue | C12N 9/1217 435/252.32 |
| 2018/0195097 A1 | 7/2018 | Lee et al. | |
| 2018/0258452 A1 | 9/2018 | Byun et al. | |
| 2020/0347419 A1 | 11/2020 | Wen et al. | |

FOREIGN PATENT DOCUMENTS

| | | |
|---|---|---|
| CN | 1582300 | 2/2005 |
| CN | 101883853 | 11/2010 |
| CN | 102021154 | 4/2011 |
| CN | 102471758 | 5/2012 |
| CN | 103243042 | 3/2016 |
| CN | 106086102 | 11/2016 |
| CN | 109536428 | 3/2019 |
| CN | 110129247 | 8/2019 |
| EP | 2107128 | 10/2009 |
| EP | 2102337 | 8/2011 |
| KR | 1020070058259 | 6/2007 |
| RU | 2683551 | 3/2019 |
| RU | 2685482 | 4/2019 |
| WO | WO 2019085445 | 5/2019 |

OTHER PUBLICATIONS

Singh et al. Curr Protein Pept Sci. 2017, 18, 1-11 (Year: 2017).*
Chica et al. Curr Opin Biotechnol. Aug. 2005;16(4):378-84. (Year: 2005).*
Accession AAG91001. Jun. 15, 2007 (Year: 2007).*
U.S. Pat. No. 20070042474. SEQ ID No. 2573 alignment. Feb. 22, 2007 (Year: 2007).*
GenBank Accession No. WP_011014143.1, "(2Fe-2S)-binding protein [Corynebacterium glutamicum]," Jul. 8, 2018, 1 page.
International Search Report in International Appln. No. PCT/CN2021/071517, dated Apr. 15, 2021, 10 pages (with English Translation).
Liu et al., "Development of a CRISPR/Cas9 genome editing toolbox for Corynebacterium glutamicum," Microb. Cell Fact., Nov. 2017, 16:205, 17 pages.
Muller et al., "FhuF, an iron-regulated protein of *Escherichia coli* with a new type of [2Fe-2S] center," Eur. J. Biochem., Dec. 1998, 258(3):1001-1008.

(Continued)

Primary Examiner — Christian L Fronda
(74) Attorney, Agent, or Firm — Fish & Richardson P.C.

(57) ABSTRACT

Provided are *Corynebacterium glutamicum* that produces L-lysine, a method for constructing the L-lysine producing strain, and a method for producing L-lysine from the strain. The lysine yield and glucose conversion of the L-lysine producing strain are improved, thereby reducing the production cost.

14 Claims, No Drawings
Specification includes a Sequence Listing.

(56) References Cited

OTHER PUBLICATIONS

Office Action in Chinese Appln. No. 202010042203.2, dated Nov. 5, 2021, 9 pages (with English Translation).
Office Action in Chinese Appln. No. 202010042203.2, dated Sep. 2, 2021, 9 pages (with English Translation).
Qiu et al., "The *Escherichia coli* polB Locus Is Identical to dinA, the Structural Gene for DNA Polymerase," J. Biol. Chem, Mar. 1997, 272(13):8611-8617.
Wang et al., "Expanding targeting scope, editing window, and base transition capability of base editing in Corynebacterium glutamicum," Biotechnol. Bioeng., Nov. 2019, 116(11):3016-3029.
Xu et al., "Metabolic engineering Corynebacterium glutamicum for the l-lysine production by increasing the flux into l-lysine biosynthetic pathway," Amino Acids, May 2014, 46(9):2165-2175.
Zhang et al., "A new genome-scale metabolic model of Corynebacterium glutamicum and its application," Biotechnol Biofuels, Jun. 2017, 10(1):169, 16 pages.
Zhou et al., "Opportunities and Challenges in the Development of Lysine Industry," Biotechnology & Business, Jan. 2019, 1:84-90 (English Abstract).
Liu et al., "Studies on enzyme inhibitor produced by microorganisms-I. Discussion on Screening Methods of Protease Inhibitors," Fujian Institute of Microbiology, Fuzhou University, Apr. 13, 1983, 8(5):275-279 (with English abstract).

\* cited by examiner

METHOD FOR PRODUCING LYSINE FROM MICROORGANISM AND FOR CONSTRUCTING MICROORGANISM

CROSS-REFERENCE TO RELATED APPLICATIONS

This application is a U.S. National Phase application under 35 U.S.C. § 371 of International Patent Application No. PCT/CN2021/071517, filed on Jan. 13, 2021, which claims priority to Chinese Application No. 202010042203.2, filed on Jan. 15, 2020. The entire contents of the parent applications are hereby incorporated by reference.

TECHNICAL FIELD

The present disclosure relates to the field of biotechnology. Specifically, the present disclosure relates to high L-lysine producing strains and construction methods and use for the same.

SEQUENCE LISTING

This application contains a Sequence Listing that has been submitted electronically as an ASCII text file named "54397-0003US1_SL_ST25.txt." The ASCII text file, created on Nov. 15, 2022, is 5,874 bytes in size. The material in the ASCII text file is hereby incorporated by reference in its entirety.

BACKGROUND

L-lysine, lysine for short, is the most important essential amino acid in human and animal nutrition and is widely used in industries such as medicine, health, food, animal feed, and cosmetics. Lysine is mainly produced by microbial fermentation. At present, the main production strains include microorganisms such as *Escherichia coli* and *Corynebacterium glutamicum*. Due to the physiological superiority of *Corynebacterium glutamicum*, it has become the most important production strain in industry. With the constant development of the biotechnology, methods for metabolic engineering of *Corynebacterium glutamicum* to improve its lysine yield have also been constantly emerging in recent years, which include modifications of synthetic pathways of lysine, weakening of synthetic competition pathways of lysine, and so forth. The capacity of lysine producing strains in industry scale has currently reached a higher level.

However, in industry, there still remains a need for strains with a higher production capacity (yield and conversion) in order to further reduce production costs. Therefore, there is an urgent need in the art for new methods for constructing lysine producing strains, so as to further improve the yield of lysine.

SUMMARY

An objective of the present disclosure is to provide a new lysine producing strain, a construction method for the strain, and a method for producing lysine by the constructed lysine producing strain.

In the first aspect, the present disclosure provides an L-lysine producing strain, wherein compared to a wild-type strain containing an endogenous polypeptide, the L-lysine producing strain has at least one of the following characteristics (i) to (iii):

(i) a reduced or disappeared polypeptide activity of the endogenous polypeptide;
(ii) a reduced or disappeared expression level of a coding gene of the endogenous polypeptide;
(iii) a reduced or disappeared expression level of a polynucleotide of interest;
the endogenous polypeptide is a polypeptide having an amino acid sequence shown in SEQ ID NO: 1, or a polypeptide encoded by a sequence having at least 90%, optionally at least 95%, preferably at least 97%, more preferably at least 98%, and most preferably at least 99% sequence identity to the amino acid sequence shown in SEQ ID NO: 1; and
the polynucleotide of interest is a polynucleotide having a nucleotide sequence shown in SEQ ID NO: 2, or a polynucleotide encoded by a sequence having at least 90%, optionally at least 95%, preferably at least 97%, more preferably at least 98%, and most preferably at least 99% sequence identity to the nucleotide sequence shown in SEQ ID NO: 2.

In a specific embodiment, in the strain, a polypeptide having 98% or more homology to the polypeptide shown in SEQ ID NO: 1 and having an FhuF domain at C-terminus is inactivated.

In a specific embodiment, the strain is *Corynebacterium glutamicum*.

In a specific embodiment, the polypeptide shown in SEQ ID NO: 1 in the strain is inactivated.

In a specific embodiment, the inactivation of the polypeptide means that compared to the endogenous polypeptide, transcription or expression of the coding gene of the polypeptide is reduced by at least 30%, preferably at least 40%, more preferably at least 50%, for example, at least 60%, at least 70%, at least 80%, at least 90%, at least 95%, at least 96%, at least 97%, at least 98%, or at least 99%, or the coding gene of the polypeptide is knocked out; or an activity of the polypeptide is reduced by at least 30%, preferably at least 40%, more preferably at least 50%, for example, at least 60%, at least 70%, at least 80%, at least 90%, at least 95%, at least 96%, at least 97%, at least 98%, or at least 99%.

In a preferred embodiment, compared to the L-lysine producing strain containing the endogenous polypeptide, an L-lysine yield of the L-lysine producing strain is increased by at least 5%, preferably at least 15%, more preferably at least 20%, more preferably at least 25%, more preferably at least 30%, and most preferably at least 35%.

In a preferred embodiment, compared to the L-lysine producing strain containing the endogenous polypeptide, the L-lysine producing strain has a glucose conversion increased by at least 10%, preferably 20%, and more preferably 30% in the process of producing L-lysine.

In a preferred embodiment, the endogenous polypeptide may be inactivated by one or a combination of the following methods: partial knockout or complete knockout of the coding gene of the polypeptide; mutations of the coding gene; alterations of promoters, or codons in the translational regulatory region or the coding region of the coding gene to attenuate the transcription or translation thereof; alterations of the sequence of the coding gene to diminish its mRNA stability or destabilize the structure of the protein it encodes; or any other means to inactivate the endogenous polypeptide by modifying the coding region of the gene and the upstream and downstream regions adjacent thereto, etc.

In a preferred embodiment, the coding sequence of the gene is caused to undergo a frameshift mutation, a missense mutation, a deletion, an alteration of the initiation codon, etc.

In a preferred embodiment, one or more genes selected from the group consisting of the following genes of the lysine-producing strain are enhanced or overexpressed:
- $a_1$. an lysC gene encoding an aspartate kinase that relieves feedback inhibition of lysine;
- $b_1$. a dapA gene encoding a dihydrodipyridine synthase that relieves feedback inhibition of lysine;
- $c_1$. a dapB gene encoding a dihydrodipicolinate reductase;
- $d_1$. a ddh gene encoding a diaminopimelate dehydratase;
- $e_1$. dapD encoding a tetrahydrodipicolinate succinylase and dapE encoding a succinyldiaminopimelate deacylase;
- $f_1$. an asd gene encoding an aspartate-semialdehyde dehydratase;
- $g_1$. a ppc gene encoding a phosphoenolpyruvate carboxylase; or
- $h_1$. a pntAB gene encoding a niacinamide adenine dinucleotide transhydrogenase.

In a preferred embodiment, one or more genes selected from the group consisting of the following genes of the strain are attenuated or the expressions thereof are reduced:
- $a_2$. an adhE gene encoding an ethanol dehydratase;
- $b_2$. an ackA gene encoding an acetate kinase;
- $c_2$. a pta gene encoding a phosphate acetyltransferase;
- $d_2$. an ldhA gene encoding a lactate dehydratase;
- $e_2$. a focA gene encoding a formate transporter;
- $f_2$. a pflB gene encoding a pyruvate formate lyase;
- $g_2$. a poxB gene encoding a pyruvate oxidase;
- $h_2$. a thrA gene encoding an aspartate kinase I/homoserine dehydratase I as a bifunctional enzyme;
- $i_2$. a thrB gene encoding a homoserine kinase;
- $j_2$. an ldcC gene encoding a lysine decarboxylase; and
- $h_2$. a cadA gene encoding a lysine decarboxylase.

In the second aspect, the present disclosure provides a construction method for an L-lysine producing strain, comprising the steps of:
  modifying a wild-type strain containing an endogenous polypeptide to reduce or disappear a polypeptide activity of the endogenous polypeptide of the wild-type strain; or
  modifying a wild-type strain containing an endogenous polypeptide to reduce or disappear an expression level of a coding gene of the endogenous polypeptide of the wild-type strain; or
  modifying a wild-type strain to reduce or disappear an expression level of a polynucleotide of interest in the wild-type strain,
  wherein the endogenous polypeptide is a polypeptide having an amino acid sequence shown in SEQ ID NO:1, or a polypeptide encoded by a sequence having at least 90%, optionally at least 95%, preferably at least 97%, more preferably at least 98%, and most preferably 99% sequence identity to the amino acid sequence shown in SEQ ID NO:1; and
  the polynucleotide of interest is a polynucleotide having a nucleotide sequence shown in SEQ ID NO: 2, or a polynucleotide encoded by a sequence having at least 90%, optionally at least 95%, preferably at least 97%, more preferably at least 98%, and most preferably 99% sequence identity to the nucleotide sequence shown in SEQ ID NO: 2.

In a specific embodiment, the strain is modified, wherein a polypeptide having 98% or more homology to the polypeptide shown in SEQ ID NO: 1 and having an FhuF domain at C-terminus is inactivated.

In a specific embodiment, the strain is *Corynebacterium glutamicum*.

In a specific embodiment, the strain is modified, wherein the polypeptide shown in SEQ ID NO: 1 is inactivated.

In a specific embodiment, the inactivation of the polypeptide means that compared to the endogenous polypeptide, transcription or expression of the coding gene of the polypeptide is reduced by at least 30%, preferably at least 40%, more preferably at least 50%, for example, at least 60%, at least 70%, at least 80%, at least 90%, at least 95%, at least 96%, at least 97%, at least 98%, or at least 99%, or the coding gene of the polypeptide is knocked out; or an activity of the polypeptide is reduced by at least 30%, preferably at least 40%, more preferably at least 50%, for example, at least 60%, at least 70%, at least 80%, at least 90%, at least 95%, at least 96%, at least 97%, at least 98%, or at least 99%.

In a preferred embodiment, compared to the L-lysine producing strain containing the endogenous polypeptide, an L-lysine yield of the L-lysine producing strain is increased by at least 5%, preferably at least 15%, more preferably at least 20%, more preferably at least 25%, more preferably at least 30%, and most preferably at least 35%.

In a preferred embodiment, compared to the L-lysine producing strain containing the endogenous polypeptide, the L-lysine producing strain has a glucose conversion increased by at least 10%, preferably 20%, and more preferably 30% in the process of producing L-lysine.

In a preferred embodiment, the endogenous polypeptide may be inactivated by one or a combination of the following methods: partial knockout or complete knockout of the coding gene of the polypeptide; mutations of the coding gene; alterations of promoters, or codons in the translational regulatory region or the coding region of the coding gene to attenuate the transcription or translation thereof; alterations of the sequence of the coding gene to diminish its mRNA stability or destabilize the structure of the protein it encodes; or any other means to inactivate the endogenous polypeptide by modifying the coding region of the gene in the cell and the upstream and downstream regions adjacent thereto, etc.

In a preferred embodiment, the coding sequence of the gene of the polypeptide is caused to undergo a frameshift mutation, a missense mutation, a deletion, an alteration of the initiation codon, etc.

In a preferred embodiment, the method further comprises enhancing or overexpressing one or more genes selected from the group consisting of the following genes in the strain:
- $a_1$. an lysC gene encoding an aspartate kinase that relieves feedback inhibition of lysine;
- $b_1$. a dapA gene encoding a dihydrodipyridine synthase that relieves feedback inhibition of lysine;
- $c_1$. a dapB gene encoding a dihydrodipicolinate reductase;
- $d_1$. a ddh gene encoding a diaminopimelate dehydratase;
- $e_1$. dapD encoding a tetrahydrodipicolinate succinylase and dapE encoding a succinyldiaminopimelate deacylase;
- $f_1$. an asd gene encoding an aspartate-semialdehyde dehydratase;
- $g_1$. a ppc gene encoding a phosphoenolpyruvate carboxylase; or
- $h_1$. a pntAB gene encoding a niacinamide adenine dinucleotide transhydrogenase.

In a preferred embodiment, the method further comprises attenuating one or more genes selected from the group consisting of the following genes in the strain or reducing expressions of one or more genes selected from the group consisting of the following genes in the strain:

a$_2$. an adhE gene encoding an ethanol dehydratase;
b$_2$. an ackA gene encoding an acetate kinase;
c$_2$. a pta gene encoding a phosphate acetyltransferase;
d$_2$. an ldhA gene encoding a lactate dehydratase;
e$_2$. a focA gene encoding a formate transporter;
f$_2$. a pflB gene encoding a pyruvate formate lyase;
g$_2$. a poxB gene encoding a pyruvate oxidase;
h$_2$. a thrA gene encoding an aspartate kinase I/homoserine dehydratase I as a bifunctional enzyme;
i$_2$. a thrB gene encoding a homoserine kinase;
j$_2$. an ldcC gene encoding a lysine decarboxylase; and
h$_2$. a cadA gene encoding a lysine decarboxylase.

In the third aspect, the present disclosure provides a method for producing L-lysine, wherein the method comprises:

1) culturing the L-lysine producing strain according to the first aspect or an L-lysine producing strain constructed by the method according to the second aspect to cause the L-lysine producing strain to produce L-lysine; and
2) optionally separating the L-lysine from a culture solution obtain in step 1).

In the fourth aspect, the present disclosure provides use of the L-lysine producing strain according to the first aspect or an L-lysine producing strain produced by the method according to the second aspect in the production of L-lysine.

It should be appreciated that within the scope disclosed herein, each of the above-mentioned technical features and each of the technical features specifically described below (such as Examples) in the present disclosure may be combined with each other to constitute new or preferred technical solutions, which will not be repeated here one by one due to the limited space.

DETAILED DESCRIPTION

After extensive and intensive researches, the present disclosure has unexpectedly found a gene encoding a hypothetical protein, and found that inactivating this gene could significantly increase the yield of lysine, thereby obtaining a high-producing strain of lysine. Based on these findings, the present disclosure is completed.

Polypeptide Shown in SEQ ID NO: 1

The polypeptide shown in SEQ ID NO: 1 (MSIWKRLLVQYPRFADTLTAGQPITLEELATP EVILEAVAKGQEIFGIEQPKHAAQLWFHSLCTAIVGPAVTAMVEFDVIPSLDIRRGQLHNI DGYWFGFRPEEMLVDASLHLSGTQFGESIRVVIDALCAATDLRPAPLWAVASDALGIAA SGAGVEAFEEEHAREVAEALIEGMNSVNSVPSPRFNDDDYFIRAGCCMIFHSPRADFCT SCPQKR) according to the present disclosure is derived from *Corynebacterium glutamicum*, which encodes a nucleotide sequence as shown in SEQ ID NO: 2 (ATGAGCATCTGGAAACGTCTGTTAGTGCAGTACC CGCGCTTCGCCGACACCCTCACAGCCGGCCAACCCATCACGCTCGAGGAATTAGCA ACCCCGGAAGTGATCTTGGAAGCTGTTGCCAAAGGCCAAGAAATTTTCGGCATTGA GCAGCCAAAACATGCAGCACAACTCTGGTTTCACTCCCTGTGCACCGCAATTGTCG GCCCCGCCGTCACCGCCATGGTGGAATTCGATGTCATCCCCAGCCTCGACATACGTC GAGGTCAGCTGCATAACATCGACGGTTACTGGTTCGGCTTCAGGCCGGAGGAGATG CTTGTCGACGCCTCCCTCCACCTGTCGGGCACCCAATTCGGCGAGAGTATCCGCGT GGTGATTGATGCATTATGCGCTGCCACGGATCTGCGACCGGCACCCCTGTGGGCGGT TGCCTCAGATGCGTTGGGAATCGCAGCTAGCGGCGCAGGTGTCGAGGCCTTTGAAG AAGAACATGCCCGCGAGGTGGCGGAAGCCCTCATTGAAGGAATGAATAGTGTGAA CTCAGTTCCATCGCCGCGGTTTAACGACGACGATTATTTCATTCGAGCTGGATGCTG CATGATTTTCCACTCACCACGAGCTGATTTTTGCACGTCGTGCCCACAGAAGAGGT GA). The polypeptide is also annotated as a (2Fe-2S) binding protein due to the presence of an FhuF domain at the C-terminus thereof. The BLAST analysis has revealed that this polypeptide is highly conserved in different *Corynebacteria glutamicum*, and has an FhuF domain at each C-terminus. Therefore, the polypeptide has the same functions in different *Corynebacteria glutamicum*.

Definitions of Terms

Polynucleotide, generally referring to polyribonucleotide and polydeoxyribonucleotide, may be unmodified RNA or DNA, or modified RNA or DNA. The nucleotide sequence described herein may be the nucleotide sequence shown in SEQ ID NO: 2, or may be a nucleotide sequence hybridized with the nucleotide sequence shown in SEQ ID NO: 2 under stringent conditions, or may be a nucleotide sequence hybridized with a probe prepared from SEQ ID NO: 2. The term "stringent conditions" described herein refers to the conditions under which specific hybridization may occur while non-specific hybridization does not occur. For example, washing is carried out in a saline solution at a certain concentration for one time, and preferably two or three times, and the corresponding concentration is 1*SSC, 0.1% SDS, preferably 0.1*SSC, 0.1% SDS at 60° C., and more preferably 0.1*SSC, 0.1% SDS at 68° C.; the length of the probe may be selected depending upon the conditions for hybridization, usually from 100 bp to 1 kb.

The terms "polypeptide", "peptide", and "protein" are used interchangeably herein and are a polymer of amino acids of any length. The polymer may be linear or branched. It may comprise modified amino acids, and may be interrupted by non-amino acids. The term also includes amino acid polymers that have been modified (e.g., disulfide bond formation, glycosylation, lipidation, acetylation, phosphorylation, or any other manipulations, such as conjugation with a labeling component).

The term "expression" includes any steps involving the production of a polypeptide, including but not limited to: transcription, post-transcriptional modification, translation, post-translational modification, and secretion.

The terms "sequence identity" and "percent identity" used herein refer to the percentage of nucleotides or amino acids that are the same (i.e., identical) between two or more polynucleotides or polypeptides. The sequence identity between two or more polynucleotides or polypeptides may be determined by aligning the nucleotide sequences of polynucleotides or the amino acid sequences of polypeptides and scoring the number of positions at which nucleotide or amino acid residues are identical in the aligned polynucleotides or polypeptides, and comparing the number of these positions with the number of positions at which nucleotide or amino acid residues are different in the aligned polynucleotides or polypeptides. Polynucleotides may differ at one position by, e.g., containing a different nucleotide (i.e., substitution or mutation) or deleting a nucleotide (i.e., insertion or deletion of a nucleotide in one or two polynucleotides). Polypeptides may differ at one position by, e.g., containing a different amino acid (i.e., substitution or mutation) or deleting an amino acid (i.e., insertion or deletion of an amino acid in one or two polypeptides). The sequence identity may be calculated by dividing the number of positions at which nucleotide or amino acid residues are identical by the total number of nucleotide or amino acid residues in the polynucleotides or polypeptides. For example, the percent identity may be calculated by dividing the number of positions at which nucleotide or amino acid residues are identical by the total number of nucleotide or amino acid residues in the polynucleotides or polypeptides, and multiplying the result by 100.

The term "wild-type/endogenous" as used herein means that a polypeptide or polynucleotide is in an unmodified state, i.e., a natural state, in a microorganism. For example, a polypeptide, polynucleotide sequence, or microorganism that can be isolated from one source in nature and has not been intentionally modified by human in the laboratory is naturally occurring. As used herein, "naturally occurring" and "wild-type" are synonymous.

In some embodiments, the wild-type strain used herein refers to a strain containing an endogenous polypeptide that is a polypeptide having an amino acid sequence shown in SEQ ID NO: 1, or a polypeptide encoded by a sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence shown in SEQ ID NO: 1.

In a specific embodiment, the wild-type strain is *Corynebacterium glutamicum* containing the endogenous polypeptide.

In some embodiments, the present disclosure genetically modifies the wild-type strain to obtain a recombination strain having at least one of the following characteristics (i) to (iii) in comparison to the wild-type strain:
  (i) a reduced or disappeared polypeptide activity of the endogenous polypeptide;
  (ii) a reduced or disappeared expression level of a coding gene of the endogenous polypeptide; and
  (iii) a reduced or disappeared expression level of a polynucleotide;
  the endogenous polypeptide is a polypeptide having an amino acid sequence shown in SEQ ID NO: 1, or a polypeptide encoded by a sequence having at least 90%, optionally at least 95%, preferably at least 97%, more preferably at least 98%, and most preferably at least 99% sequence identity to the amino acid sequence shown in SEQ ID NO: 1; and
  the polynucleotide is a polynucleotide having a nucleotide sequence shown in SEQ ID NO: 2, or a polynucleotide encoded by a sequence having at least 90%, optionally at least 95%, preferably at least 97%, more preferably at least 98%, and most preferably at least 99% sequence identity to the nucleotide sequence shown in SEQ ID NO: 2.

Based on the teachings of the present disclosure, a person skilled in the art should appreciate that the present disclosure improves the lysine yield of the strain by inactivating the polypeptide shown in SEQ ID NO: 1 of *Corynebacterium glutamicum*. As such, the wording "the polypeptide shown in SEQ ID NO: 1 is inactivated" described herein means that compared to the wild-type strain, the expression of the polypeptide shown in SEQ ID NO: 1 is reduced, attenuated, or even completely disappeared, or means that a gene that is not expressed is produced, or although the gene is expressed, the expression product does not have an activity or has a reduced activity.

In a specific embodiment, compared to a wild-type or endogenous polypeptide, the transcription or expression of the mutated gene or the activity of the protein encoded by the mutated gene is reduced by at least 30%, preferably at least 40%, more preferably at least 50%, for example, at least 60%, at least 70%, at least 80%, at least 90%, at least 95%, at least 96%, at least 97%, at least 98%, or at least 99%, or the coding gene of the wild-type or endogenous polypeptide is knocked out.

The term "modification" used herein refers to any genetic manipulation of a wild-type strain or parental strain, including but not limited to various molecular biological means. The terms "modification", "gene editing", and "genetic modification" used herein may be interchangeable.

The term "inactivation" used herein may be realized by modifications, including but not limited to, deletion of part or all of the coding gene, frameshift mutation of the gene reading frame, attenuation of the intensity of transcription or translation, or use of a gene or allele encoding a corresponding enzyme or protein with a lower activity, or inactivation of the corresponding gene or enzyme, and optionally use of these methods in combination. The gene expression may be reduced by adopting suitable culture methods or genetic modifications (mutations) of the signal structures of gene expression. For example, signal structures of gene expression are repressor genes, active genes, operator genes, promoters, attenuators, ribosome binding sites, initiation codons, and terminators.

Based on the teachings of the present disclosure, a person skilled in the art is clear that the lysine yield may be improved by inactivating the coding gene of the polypeptide shown in SEQ ID NO: 1, or by rendering the polypeptide shown in SEQ ID NO: 1 unable to function properly in the cell. A person skilled in the art could achieve the above object by technical means known in the art. It may be achieved, for example, by making the enzyme-encoding gene defective on the chromosome, or by modifying one expression control sequence such as a promoter or SD sequence; or it may be achieved by introducing an amino acid substitution (missense mutation) or a termination codon (nonsense mutation) into the coding region, or introducing insertion or deletion of one or two bases (frameshift mutation) into the coding region or deleting a part of gene (Journal of Biological Chemistry 1997, 272: 8611-8617). The present disclosure includes but is not limited to the above methods.

"Glucose conversion" used herein refers to the molar ratio of glucose as the substrate converted to lysine as the product.

"Lysine-producing strain" used herein refers to a strain that produces lysine when bacteria are cultured in a medium and could accumulate lysine, or could secrete lysine into the medium, that is, extracellular free lysine is obtainable. For example, the strains may be naturally occurring lysine-producing strains, or may be engineered lysine-producing strains obtained by genetic modifications. The modifications include, but are not limited to, the modification that one or more genes selected from the group consisting of the following genes of the strain are enhanced or overexpressed:
  $a_1$. an lysC gene encoding an aspartate kinase that relieves feedback inhibition of lysine;
  $b_1$. a dapA gene encoding a dihydrodipyridine synthase that relieves feedback inhibition of lysine;
  $c_1$. a dapB gene encoding a dihydrodipicolinate reductase;
  $d_1$. a ddh gene encoding a diaminopimelate dehydratase;

e₁. dapD encoding a tetrahydrodipicolinate succinylase and dapE encoding a succinyldiaminopimelate deacylase;

f₁. an asd gene encoding an aspartate-semialdehyde dehydratase;

g₁. a ppc gene encoding a phosphoenolpyruvate carboxylase; and h₁. a pntAB gene encoding a niacinamide adenine dinucleotide transhydrogenase.

In addition, the modifications include, but are not limited to, the modification that one or more genes selected from the group consisting of the following genes of the strain are attenuated or the expressions thereof are reduced:

a₂. an adhE gene encoding an ethanol dehydratase;

b₂. an ackA gene encoding an acetate kinase;

c₂. a pta gene encoding a phosphate acetyltransferase;

d₂. an ldhA gene encoding a lactate dehydratase;

e₂. a focA gene encoding a formate transporter;

f₂. a pflB gene encoding a pyruvate formate lyase;

g₂. a poxB gene encoding a pyruvate oxidase;

h₂. a thrA gene encoding an aspartate kinase I/homoserine dehydratase I as a bifunctional enzyme;

i₂. a thrB gene encoding a homoserine kinase;

j₂. an ldcC gene encoding a lysine decarboxylase; and h₂. a cadA gene encoding a lysine decarboxylase.

In some embodiments, the engineered lysine-producing strains obtained by genetic modifications, which have a reduced or disappeared protein activity, a reduced or disappeared expression level of a protein-encoding gene, a reduced or disappeared enzyme activity, or a reduced or disappeared expression level of an enzyme-encoding gene, include recombinant strains modified by the following genetic engineering methods: introduction of a weak promoter or a weak ribosome binding site into a strain, gene knockout or knockdown of the coding gene of a protein or an enzyme, and insertion of a random fragment into the coding gene of a protein or an enzyme to provoke loss of the activity of the protein or enzyme.

In some embodiments, the enhanced protein activity, enhanced expression level of a protein-encoding gene, enhanced enzyme activity, or enhanced expression level of an enzyme-encoding gene in the engineered lysine-producing strains obtained by genetic modifications are realized by modifications including the following genetic engineering methods: introduction of strong promoters or strong ribosome binding sites, introduction of recombinant expression vectors of non-integral proteins or enzymes, and introduction of recombinant expression vectors of chromosomally integrated proteins or enzymes.

The term "vector" refers to a DNA construct containing DNA sequences operably linked to appropriate control sequences, so as to express a gene of interest in a suitable host. "Recombinant expression vector" refers to a DNA construct used to express, for example, a polynucleotide encoding a desired polypeptide. The recombinant expression vector may include, for example: i) a collection of genetic elements having a regulatory effect on gene expression, such as promoters and enhancers; ii) a structure or coding sequence that is transcribed into mRNA and translated into a protein; and iii) transcriptional subunits that appropriately transcribe and translate initiation and termination sequences. The recombinant expression vectors are constructed in any suitable manner. The nature of the vector is not critical, and any vector may be used, including plasmids, viruses, phages, and transposons. Potential vectors used herein include, but are not limited to, chromosomal, non-chromosomal, and synthetic DNA sequences, such as bacterial plasmids, phage DNAs, yeast plasmids, and vectors derived from combinations of plasmids and phage DNAs, and DNAs from viruses such as vaccinia, adenovirus, avian pox, baculovirus, SV40, and pseudorabies. In some embodiments, the "recombinant expression vector" used herein refers to a mutant vector.

The terms "transformation, transfection, and transduction" used herein have the meanings generally understood by a person skilled in the art, namely, a process of introducing an exogenous DNA into a host. Methods for the transformation, transfection, and transduction include any method for introducing a nucleic acid into a cell. These methods include, but are not limited to, electroporation, calcium phosphate ($CaPO_4$) precipitation, calcium chloride ($CaCl_2$)) precipitation, microinjection, a polyethylene glycol (PEG) method, a DEAE-dextran method, a cationic liposome method, and a lithium acetate-DMSO method.

The strains described herein may be cultured by conventional methods in the art, including, but not limited to, well-plate culture, shake-flask culture, batch culture, continuous culture, fed batch culture, etc. Also, various culture conditions such as the temperature, time, and pH value of the medium may be properly adjusted according to actual situations.

Unless otherwise defined or clearly indicated by context, all technical and scientific terms used herein have the same meanings as typically understood by one of ordinary skill in the art to which the present disclosure belongs.

Advantages of the Present Disclosure 1. the present disclosure provides a new method for constructing lysine-producing strains, thereby opening up new ideas for construction of high L-lysine producing strains;

2. both the lysine yield and the glucose conversion of the lysine-producing strains constructed herein are somewhat improved; and 3. the cost of producing lysine by the method described herein is somewhat reduced.

The present disclosure will be further illustrated with reference to specific examples. It should be appreciated that these examples are merely intended to illustrate the present disclosure and are not intended to limit the scope of the present disclosure. Experimental methods for which no specific conditions are indicated in the following examples are generally performed according to conventional conditions such as those described by Sambrook et al., *Molecular Cloning: A Laboratory Manual* (New York: Cold Spring Harbor Laboratory Press, 1989), or those recommended by manufacturers.

Unless otherwise defined, all technical and scientific terms used herein have the same meanings as typically understood by one of ordinary skill in the art to which the present disclosure belongs. Although any methods and materials similar or equivalent to those described herein may be used to implement or test the present disclosure, the methods and materials described herein are preferred.

Example 1. Construction of Mutant Vector of lysC Gene in *Corynebacterium glutamicum*

Due to the feedback regulation of key genes, the wild-type *Corynebacterium glutamicum* ATCC13032 could not accumulate lysine. It was reported in literatures that strains relieved of the feedback inhibition of the aspartate kinase (encoded by the lysC gene) could accumulate lysine. In view of this, the inventors first constructed a strain with some lysine synthesis capability by mutating the aspartate kinase (Thr mutated into Ile at position 311). According to the published genome sequence of *Corynebacterium glutamicum* ATCC13032, primers lysC-F1/R1 and lysC-F2/R2 were designed respectively, and upstream and downstream homologous arm fragments for lysC mutation (where the base C was mutated into T at position 932 of the lysC gene) were obtained by PCR amplification using the ATCC13032 genome as a template. The above PCR fragments were recovered, and then ligated with a pK18mobsacB vector that was enzyme digested by EcoRI and BamHI to obtain pK18-lysC as a mutant vector of the lysC gene.

Example 2. Construction of Mutant Strain of lysC Gene in *Corynebacterium glutamicum*

Competent cells of *Corynebacterium glutamicum* ATCC13032 were prepared. The pK18-lysC plasmid as constructed above was transformed into this strain. The strain was coated on an LBHIS solid medium (2.5 g/L of yeast powder, 5 g/L of peptone, 5 g/L of sodium chloride, 18.5 g/L of brain-heart infusion, 91 g/L of sorbitol) containing 25 µg/mL of kanamycin, and cultured at 30° C. to obtain the first recombinant transformants. The correct transformants were transferred into an LB medium containing 5 g/L of glucose, and cultured overnight. Thereafter, the culture was transferred into an LB medium containing 100 g/L of sucrose and cultured at 30° C. for 6 h, and then coated on an LB medium containing 100 g/L of sucrose for screening to obtain SCgL30 as a mutant strain of lysC.

Example 3. Construction of Vector with Coding Gene Knockout from Polypeptide Shown in SEQ ID NO: 1 of *Corynebacterium glutamicum*

According to the reported genome sequence of *Corynebacterium glutamicum* ATCC13032, primers SEQ ID NO: 1-F1/R1 and SEQ ID NO: 1-F2/R2 were designed respectively, and upstream and downstream homologous arms of the gene for the polypeptide shown in SEQ ID NO: 1 were obtained by PCR amplification using the ATCC13032 genome as a template. The above PCR fragments were recovered, and then ligated with a pK18mobsacB vector that was enzyme digested by EcoRI and BamHI to obtain pK18-SEQ ID NO: 1 as a mutant vector of the gene for the polypeptide shown in SEQ ID NO: 1.

Example 4. Construction of Strain with Deletion of Polypeptide Shown in SEQ ID NO: 1 of *Corynebacterium glutamicum*

Competent cells of the SCgL30 strain were prepared. The pK18-SEQ ID NO: 1 plasmid as constructed above was transformed into this strain. The strain was coated on an LBHIS solid medium containing 5 g/L of glucose and 25 µg/mL of kanamycin, and cultured at 30° C. to obtain the first recombinant transformants. The correct transformants were transferred into an LB medium containing 5 g/L of glucose, and cultured overnight. Thereafter, the culture was transferred into an LB medium containing 100 g/L of sucrose and cultured at 30° C. for 6 h, and then coated on an LB medium containing 100 g/L of sucrose for screening to obtain SCgL31 as a strain with the deletion of the polypeptide shown in SEQ ID NO: 1.

Example 5. Influence of Deletion of Polypeptide Shown in SEQ ID NO: 1 on Synthesis of Lysine from *Corynebacterium glutamicum*

In order to test how knockout of the gene for the polypeptide shown in SEQ ID NO: 1 in *Corynebacterium glutamicum* affected the production of lysine by the strain, fermentation tests were performed on SCgL30 and SCgL31, respectively. The fermentation medium was a CGXII medium with the following main ingredients (g/L): $(NH_4)_2SO_4$, 20; urea, 5; $KH_2PO_4$, 1; $K_2HPO_4·3H_2O$, 1.3; 3-(N-morpholino)propanesulfoinc acid (MOPS), 42; $CaCl_2$, 0.01; $FeSO_4·7H_2O$, 0.01; $MnSO_4·H_2O$, 0.01; $ZnSO_4·7H_2O$, 0.001; $CuSO_4$, 0.0002; $NiCl·6H_2O$, 0.00002; $MgSO_4·7H_2O$, 0.25; protocatechuic acid, 0.03; vitamin $B_1$, 0.0001; biotin, 0.0002; and glucose, 80. The strains were firstly inoculated into an LB medium containing 10 g/L of glucose, and cultured overnight. The cultures were inoculated as seeds into a 24-well plate containing 600 µl of fermentation media in each well with the initial OD controlled at 0.5, and cultured at 30° C. for 29 h. The rotating speed of the plate shaker was 800 rpm. Three samples were set for each strain. After the fermentation, the lysine yield and glucose consumption were measured. The results were listed in Table 1. Both the Lys yield and the glucose conversion were significantly improved after knockout of the polypeptide shown in SEQ ID NO: 1.

TABLE 1

| Strains | Lysine (g/L) | Conversion (mM/M*100%) |
|---|---|---|
| SCgL30 | 3.80 | 59.40 |
| SCgL31 | 4.20 | 65.32 |

Example 6. Construction of Strain with Attenuated Polypeptide SEQ ID NO: 1 Based on dCas9

First of all, the Cas9 gene of the pCas9 (LIU, Jiao, et al. Development of a CRISPR/Cas9 genome editing toolbox for *Corynebacterium glutamicum*. Microbial cell factories, 2017, 16.1: 205) plasmid was mutated at D10A and H840A, while removing the BsaI restriction enzyme cutting site from the plasmid backbone to obtain a pdCas9 plasmid. Thereafter, a gRNA-ccdB expression cassette was amplified from the pnCas9(D10A)-AID-gRNA-ccdBTS (WANG, Yu, et al. Expanding targeting scope, editing window, and base transition capability of base editing in *Corynebacterium glutamicum*. Biotechnology and bioengineering, 2019, 116: 3016-3029) plasmid and cloned into the same position of pdCas9 to obtain pdCas9gRNA-ccdB as a CRISPRi plasmid that could be efficiently constructed.

The above dCas9-based attenuated system was utilized to construct an attenuated vector of the polypeptide shown in SEQ ID NO: 1 and a control vector thereof. According to the reported genome sequence of *Corynebacterium glutamicum* ATCC13032, primers dCas-F/R were designed, respectively. The two primers were denatured and annealed to obtain complementary fragments. The above fragments were ligated with the pdCas9-ccdB plasmid that was enzyme digested by BsaI via Goldengate to construct pdCas-SEQ ID NO: 1 as the attenuated vector with the gRNA of the polypeptide shown in SEQ ID NO: 1. According to the sequence of pdCas9gRNA-ccdB, primers Cas-1, Cas-2, Cas-3, and Cas-4 were designed. Two plasmid fragments were obtained by PCR amplification, and recombined by Vazyme as a recombinase to obtain pdCas9 as a control vector without any complementary regions on gRNA. The above-mentioned recombinant vectors pdCas-SEQ ID NO: 1 and pdCas9 were transformed into the SCgL30 strains respectively to obtain SCgL30/pdCas-SEQ ID NO: 1 as the attenuated strain of the polypeptide shown in SEQ ID NO: 1 and SCgL30/pdCas9 as the control strain.

Example 7. Influence of Attenuation of Polypeptide Shown in SEQ ID NO: 1 on Synthesis of Lysine from *Corynebacterium glutamicum*

In order to test how attenuation of the gene expression of the polypeptide shown in SEQ ID NO: 1 in *Corynebacterium glutamicum* affected the production of lysine by the strain, fermentation tests were performed on SCgL30/pdCas9 and SCgL30/pdCas-SEQ ID NO: 1, respectively. The ingredients of the fermentation medium were as follows (g/L): glucose, 80; yeast powder, 8; urea, 9; $K_2HPO_4$, 1.5; $MnSO_4$, 0.01; $MgSO_4$, 0.6; $FeSO_4$, 0.01; and MOPS, 42. The strains were firstly inoculated into an LB medium containing 10 g/L of glucose, and cultured overnight. The cultures were inoculated as seeds into a 24-well plate containing 600 μl of fermentation media in each well with the initial OD controlled at 0.5, and cultured at 30° C. for 29 h. The rotating speed of the plate shaker was 800 rpm. Three samples were set for each strain. After the fermentation, the lysine yield and glucose consumption were measured. The results were listed in Table 2. Both the Lys yield and the glucose conversion were significantly improved after the polypeptide shown in SEQ ID NO: 1 was attenuated. The RT-PCR test results showed that the transcriptional level of the polypeptide shown in SEQ ID NO: 1 in the strain SCgL30/pdCas-SEQ ID NO: 1 was reduced by 31% in comparison to that in the control strain.

TABLE 2

| Strains | Lysine (g/L) | Conversion (mM/M*100%) |
| --- | --- | --- |
| SCgL30/pdCas9 | 1.33 | 23.15 |
| SCgL30/pdCas-SEQ ID NO: 1 | 1.67 | 30.00 |

Example 8. Application of Deletion of Polypeptide Shown in SEQ ID NO: 1 in High Lysine Producing Strains (1) Construction of a Strain with Deletion of the Polypeptide Shown in SEQ ID NO: 1 In a High Lysine Producing Strain The pK18mobsacB-based homologous recombination technique was utilized to mutate the threonine at position 311 of the aspartate kinase (encoded by the lysC gene) on the *Corynebacterium glutamicum* ATCC13032 genome into isoleucine, to mutate the core region sequence at positions 279 to 317 of the gene promoter of the pyruvate carboxylase (encoded by the pyc gene) from CGATGTTTGATTGGGG-GAATCGGGGGTTACGATACTAGG to CGGGCCTT-GATTGTAAGATAAGACATTTAGTATAATTAG, and to mutate the core region sequence at positions 292 to 300 of the gene promoter of the diaminopimelate dehydrogenase (encoded by the ddh gene) from ATGCATCTC to CCTTGT-TAT, to construct SCgL40 as a high lysine producing strain. Competent cells of the SCgL40 strain were prepared. The pK18-SEQ ID NO: 1 plasmid as constructed above was transformed into this strain. The strain was coated on an LBHIS medium containing 5 g/L of glucose and 25 μg/mL of kanamycin, and cultured at 30° C. for 6 h. Thereafter, the culture was coated on an LB medium containing 100 g/L of sucrose for screening to obtain SCgL31 as the strain with the deletion of the polypeptide shown in SEQ ID NO: 1.

(2) Influence of Deletion of Polypeptide Shown in SEQ ID NO: 1 on Synthesis of Lysine By High-Producing Strains In order to test how deletion of the polypeptide shown in SEQ ID NO: 1 affected the production of L-lysine by the high-producing strain, fermentation tests were performed on SCgL45 and SCgL40, respectively. The ingredients of the fermentation medium were as follows (g/L): glucose, 80 g/L; yeast powder, 1 g/L; soy peptone, 1 g/L; NaCl, 1 g/L; ammonium sulfate, 1 g/L; urea, 10 g/L; $K_2HPO_4·3H_2O$, 1 g/L; $MgSO_4·7H_2O$, 0.45 g/L; $FeSO_4·7H_2O$, 0.05 g/L; biotin, 0.4 mg/L; vitamin B1, 0.1 mg/L; MOPS, 40 g/L; initial pH7.2. The strains were firstly inoculated into a TSB liquid medium, and cultured for 8 h. The cultures were inoculated as seeds into a 24-well plate containing 800 μl of fermentation media in each well with the initial $OD_{600}$ controlled at about 0.1, and cultured at 30° C. for 21 h. The rotating speed of the plate shaker was 800 rpm. Three samples were set for each strain. After the fermentation, the L-lysine yield and glucose consumption were measured, and the conversion from glucose to saccharic acid of L-lysine was calculated. The ingredients of the TSB medium were as follows (g/L): glucose, 5 g/L; yeast powder, 5 g/L; soy peptone, 9 g/L; urea, 3 g/L; succinic acid, 0.5 g/L; $K_2HPO_4·3H_2O$, 1 g/L; $MgSO_4·7H_2O$, 0.1 g/L; biotin, 0.01 mg/L; vitamin B1, 0.1 mg/L; and MOPS, 20 g/L. The results were listed in Table 3. Both the lysine yield and the saccharic acid conversions of the strains were significantly improved after the polypeptide shown in SEQ ID NO: 1 was deleted.

TABLE 3

| Strains | Lysine (g/L) | Conversion (mM/M*100%) |
| --- | --- | --- |
| SCgL40 | 6.07 | 74.07 |
| SCgL45 | 8.53 | 122.16 |

In order to further confirm the effect resulting from the deletion of the polypeptide shown in SEQ ID NO: 1 in high-producing strains, the above-mentioned two strains were subjected to the fermentation tests in 5 L fermenters. The ingredients of the fermentation medium were as follows (g/L): glucose, 60 g/L; molasses, 15 g/L; corn plasm, 1.5 g/L; KCl, 0.5 g/L; ammonium sulfate, 20 g/L; phosphoric acid, 0.5 g/L; ferrous sulfate, 150 mg/L; manganese sulfate, 150 mg/L; $MgSO_4·7H_2O$, 1 g/L; biotin, 1 mg/L; vitamin B1, 5 mg/L; fed-batch glucose mother liquor and ammonium sulfate mother liquor. The strains were firstly activated in TSB solid media, and inoculated into TSB liquid media and cultured for 12 h. 200 ml of the above cultures were inoculated as seeds into 5 L fermenters containing 1.8 L fermentation media, and fermented at 37° C. for 24 h. The L-lysine yield was tested during fermentation. The fermentation results showed that the lysine yield of the strain SCgL40 after fermented for 24 h was 30 g/L, whereas the lysine yield of the strain SCgL45 with the deletion of the polypeptide shown in SEQ ID NO: 1 reached 48 g/L, which was improved very significantly.

The primers used in the present Examples were listed in the table below:

| SEQ ID NO | Name | Sequence (5'-3') |
|---|---|---|
| 3 | lysC-F1 | ATGACATGATTACGAATTCACACTCCTCTGGCTAGGTAG |
| 4 | lysC-R1 | ATGATGTCGGTGGTGCCGTCT |
| 5 | lysC-F2 | ACGGCACCACCGACATCATCTTCACCTGCCCTCGTTCC |
| 6 | lysC-R2 | GGTCGACTCTAGAGGATCCACGCAGGTGCCTGAGACCTT |
| 7 | SEQ ID NO: 1-F1 | ATGACATGATTACGAATTCATCTCTGTGCACTCATCTAC |
| 8 | SEQ ID NO: 1-R1 | TGCTAATTCCTCGAGCGTGA |
| 9 | SEQ ID NO: 1-F2 | CACGCTCGAGGAATTAGCACGAGCTGGATGCTGCATGAT |
| 10 | SEQ ID NO: 1-R2 | AGTTATTGGTGCCCTTCGATTCCAAAAGTGCAGCCTAGA |
| 11 | dCas-F | TTCATGCTAATTCCTCGAGCGTGA |
| 12 | dCas-R | AAACTCACGCTCGAGGAATTAGCA |
| 13 | Cas-1 | ACAGGTACAGTGTAATTCAGTTTTAGAGCTAGAAATAGC |
| 14 | Cas-2 | TCAGTCACCTCCTAGCTGAC |
| 15 | Cas-3 | GTCAGCTAGGAGGTGACTGA |
| 16 | Cas-4 | TGAATTACACTGTACCTGTT |

Example 9. Comparison of Homologies of Polypeptide Shown in SEQ ID NO: 1 in Different *Corynebacteria glutamicum*

The sequence alignment and analysis of the polypeptide shown in SEQ ID NO: 1 was carried out based on the NCBI database. The results showed that the DNA sequence identity and the amino acid sequence identity of this polypeptide in different *Corynebacteria glutamicum* reached 98.01% and 98.56% or more respectively, indicating that the polypeptide was highly conserved in *Corynebacterium glutamicum*. In addition, the sequence analysis showed that the protein contained a C-terminus domain of FhuF (a 2Fe-2S-containing iron reductase in the *Escherichia coli* cytoplasm) at the C-terminus, and this domain was present in all of the homologous sequences in the above *Corynebacteria glutamicum*. Therefore, either deletion or attenuation of the above homologous genes in different *Corynebacteria glutamicum* was conducive to synthesis of lysine.

All documents referred to herein are incorporated herein by reference just as each of the documents is incorporated by reference individually. It should be appreciated here that after reading the content described above, a person skilled in the art may make various alterations or modifications to the present disclosure, and these equivalents also fall within the scope defined by the claims appended to the present disclosure.

What is claimed is:

1. An L-lysine producing bacterium *Corynebacterium glutamicum*, wherein, compared to a wild-type bacterium containing an endogenous polypeptide, the L-lysine producing bacterium has at least one of the following characteristics (i) to (iii):
   (i) a reduced or eliminated polypeptide activity of the endogenous polypeptide;
   (ii) a reduced or eliminated expression level of a coding gene of the endogenous polypeptide; and
   (iii) a reduced or eliminated expression level of a polynucleotide of interest;

wherein by having at least one of the characteristics (i) to (iii), L-lysine production in the L-lysine producing bacterium *Corynebacterium glutamicum* is increased as compared to that in the wild-type bacterium, wherein the endogenous polypeptide is a polypeptide having the amino acid sequence of SEQ ID NO: 1, or a polypeptide having at least 90% sequence identity to the amino acid sequence of SEQ ID NO: 1; and the polynucleotide of interest is a polynucleotide having the nucleotide sequence of SEQ ID NO: 2, or a polynucleotide having at least 90% sequence identity to the nucleotide sequence of SEQ ID NO: 2.

2. The L-lysine producing bacterium *Corynebacterium glutamicum* according to claim 1, wherein, in said bacterium, a polypeptide having 98% or more homology to the polypeptide of SEQ ID NO: 1 and having an FhuF domain at C-terminus is inactivated.

3. The L-lysine producing bacterium *Corynebacterium glutamicum* according to claim 1, wherein, in said bacterium, the polypeptide of SEQ ID NO: 1 is inactivated.

4. The L-lysine producing bacterium *Corynebacterium glutamicum* according to claim 3, wherein the inactivation of the polypeptide means that compared to the endogenous polypeptide, transcription or expression of the coding gene of the polypeptide is reduced by at least 30%, or the coding gene of the polypeptide is knocked out; or an activity of the polypeptide is reduced by at least 30%.

5. The L-lysine producing bacterium *Corynebacterium glutamicum* according to claim 1, wherein compared to the wild-type bacterium containing the endogenous polypeptide, an L-lysine yield of the L-lysine producing bacterium is increased by at least 5%.

6. The L-lysine producing bacterium *Corynebacterium glutamicum* according to claim 1, wherein one or more genes selected from the group consisting of the following genes of the L-lysine producing bacterium are overexpressed:
   $a_1$. a lysC gene encoding an aspartate kinase that relieves feedback inhibition of lysine;
   $b_1$. a dapA gene encoding a dihydrodipyridine synthase that relieves feedback inhibition of lysine;
   $c_1$. a dapB gene encoding a dihydrodipicolinate reductase;
   $d_1$. a ddh gene encoding a diaminopimelate dehydratase;
   $e_1$. a dapD gene encoding a tetrahydrodipicolinate succinylase and a dapE gene encoding a succinyl-diaminopimelate deacylase;
   $f_1$. an asd gene encoding an aspartate-semialdehyde dehydratase;
   $g_1$. a ppc gene encoding a phosphoenolpyruvate carboxylase; and
   $h_1$. a pntAB gene encoding a niacinamide adenine dinucleotide transhydrogenase;
   optionally, one or more genes selected from the group consisting of the following genes of the L-lysine producing bacterium are attenuated or the expressions thereof are reduced:
   $a_2$. an adhE gene encoding an ethanol dehydratase;
   $b_2$. an ackA gene encoding an acetate kinase;
   $c_2$. a pta gene encoding a phosphate acetyltransferase;
   $d_2$. an ldhA gene encoding a lactate dehydratase;
   $e_2$. a focA gene encoding a formate transporter;
   $f_2$. a pflB gene encoding a pyruvate formate lyase;
   $g_2$. a poxB gene encoding a pyruvate oxidase;
   $h_2$. a thrA gene encoding an aspartate kinase I/homoserine dehydratase I as a bifunctional enzyme;
   $i_2$. A thrB gene encoding a homoserine kinase;
   $j_2$. an ldcC gene encoding a lysine decarboxylase; and
   $k_2$. a cadA gene encoding a lysine decarboxylase.

7. A method for constructing an L-lysine producing bacterium *Corynebacterium glutamicum*, wherein the method comprises:
   modifying a wild-type bacterium containing an endogenous polypeptide to reduce or eliminate a polypeptide activity of the endogenous polypeptide of the wild-type bacterium;
   modifying a wild-type bacterium containing an endogenous polypeptide to reduce or eliminate an expression level of a coding gene of the endogenous polypeptide of the wild-type bacterium; or
   modifying a wild-type bacterium to reduce or eliminate an expression level of a polynucleotide of interest in the wild-type bacterium;
   wherein by modifying the wild-type bacterium, L-lysine production in the L-lysine producing bacterium *Corynebacterium glutamicum* is increased as compared to that in the wild-type bacterium,
   wherein the endogenous polypeptide is a polypeptide having the amino acid sequence of SEQ ID NO: 1, or a polypeptide having at least 90% sequence identity to the amino acid sequence of SEQ ID NO: 1; and
   the polynucleotide of interest is a polynucleotide having the nucleotide sequence of SEQ ID NO: 2, or a polynucleotide having at least 90% sequence identity to the nucleotide sequence of SEQ ID NO: 2.

8. The method according to claim 7, wherein the bacterium is modified, and wherein a polypeptide having 98% or more homology to the polypeptide of SEQ ID NO: 1 and having an FhuF domain at C-terminus is inactivated.

9. The method according to claim 7, wherein the bacterium is modified, and wherein the polypeptide of SEQ ID NO: 1 is inactivated.

10. The method according to claim 8, wherein the inactivation of the polypeptide means that compared to the endogenous polypeptide, transcription or expression of the coding gene of the polypeptide is reduced by at least 30%, or the coding gene of the polypeptide is knocked out; or
    the reduction or elimination of the activity of the polypeptide means that the activity of the polypeptide is reduced by at least 30%.

11. The method according to claim 7, wherein the method further comprises overexpressing one or more genes selected from the group consisting of the following genes in the bacterium:
    $a_1$. an lysC gene encoding an aspartate kinase that relieves feedback inhibition of lysine;
    $b_1$. a dapA gene encoding a dihydrodipyridine synthase that relieves feedback inhibition of lysine;
    $c_1$. a dapB gene encoding a dihydrodipicolinate reductase;
    $d_1$. a ddh gene encoding a diaminopimelate dehydratase;
    $e_1$. a dapD gene encoding a tetrahydrodipicolinate succinylase and a dapE gene encoding a succinyl-diaminopimelate deacylase;
    $f_1$. an asd gene encoding an aspartate-semialdehyde dehydratase;
    $g_1$. a ppc gene encoding a phosphoenolpyruvate carboxylase; and
    $h_1$. a pntAB gene encoding a niacinamide adenine dinucleotide transhydrogenase;
    optionally, the method further comprises attenuating one or more genes selected from the group consisting of the following genes in the bacterium or reducing expressions of one or more genes selected from the group consisting of the following genes in the bacterium:
    $a_2$. an adhE gene encoding an ethanol dehydratase;
    $b_2$. an ackA gene encoding an acetate kinase;
    $c_2$. a pta gene encoding a phosphate acetyltransferase;
    $d_2$. an ldhA gene encoding a lactate dehydratase;
    $e_2$. a focA gene encoding a formate transporter;
    $f_2$. a pflB gene encoding a pyruvate formate lyase;
    $g_2$. a poxB gene encoding a pyruvate oxidase;
    $h_2$. a thrA gene encoding an aspartate kinase I/homoserine dehydratase I as a bifunctional enzyme;
    $i_2$. A thrB gene encoding a homoserine kinase;
    $j_2$. an ldcC gene encoding a lysine decarboxylase; and
    $k_2$. a cadA gene encoding a lysine decarboxylase.

12. A method for producing L-lysine, wherein the method comprises:
1) Culturing the L-lysine producing bacterium *Corynebacterium glutamicum* according to claim 1 to produce L-lysine; and
2) optionally separating the L-lysine from a culture obtain in step 1).

13. A method for producing L-lysine, wherein the method comprises:
1) Culturing the L-lysine producing bacterium *Corynebacterium glutamicum* constructed by the method according to claim 8 to produce L-lysine; and
2) optionally separating the L-lysine from a culture obtain in step 1).

14. The L-lysine producing bacterium *Corynebacterium glutamicum* according to claim 1, wherein glucose conversion in the L-lysine producing bacterium *Corynebacterium glutamicum* is increased by at least 10%, compared to that in the wild-type bacterium containing the endogenous polypeptide.

* * * * *

SEQUENCE LISTING

<160> NUMBER OF SEQ ID NOS: 16

<210> SEQ ID NO 1
<211> LENGTH: 217
<212> TYPE: PRT
<213> ORGANISM: Artificial Sequence
<220> FEATURE:
<223> OTHER INFORMATION: synthetic

<400> SEQUENCE: 1

Met Ser Ile Trp Lys Arg Leu Leu Val Gln Tyr Pro Arg Phe Ala Asp
1               5                   10                  15

Thr Leu Thr Ala Gly Gln Pro Ile Thr Leu Glu Glu Leu Ala Thr Pro
            20                  25                  30

Glu Val Ile Leu Glu Ala Val Ala Lys Gly Gln Glu Ile Phe Gly Ile
        35                  40                  45

Glu Gln Pro Lys His Ala Ala Gln Leu Trp Phe His Ser Leu Cys Thr
    50                  55                  60

Ala Ile Val Gly Pro Ala Val Thr Ala Met Val Glu Phe Asp Val Ile
65                  70                  75                  80

Pro Ser Leu Asp Ile Arg Arg Gly Gln Leu His Asn Ile Asp Gly Tyr
                85                  90                  95

Trp Phe Gly Phe Arg Pro Glu Glu Met Leu Val Asp Ala Ser Leu His
                100                 105                 110

Leu Ser Gly Thr Gln Phe Gly Glu Ser Ile Arg Val Val Ile Asp Ala
    115                 120                 125

Leu Cys Ala Ala Thr Asp Leu Arg Pro Ala Pro Leu Trp Ala Val Ala
130                 135                 140

Ser Asp Ala Leu Gly Ile Ala Ala Ser Gly Ala Gly Val Glu Ala Phe
145                 150                 155                 160

Glu Glu Glu His Ala Arg Glu Val Ala Glu Ala Leu Ile Glu Gly Met
                165                 170                 175

Asn Ser Val Asn Ser Val Pro Ser Pro Arg Phe Asn Asp Asp Asp Tyr
            180                 185                 190

Phe Ile Arg Ala Gly Cys Cys Met Ile Phe His Ser Pro Arg Ala Asp
        195                 200                 205

Phe Cys Thr Ser Cys Pro Gln Lys Arg
    210                 215

<210> SEQ ID NO 2
<211> LENGTH: 654
<212> TYPE: DNA
<213> ORGANISM: Artificial Sequence
<220> FEATURE:
<223> OTHER INFORMATION: synthetic

<400> SEQUENCE: 2
atgagcatct ggaaacgtct gttagtgcag tacccgcgct tcgccgacac cctcacagcc      60
ggccaaccca tcacgctcga ggaattagca accccggaag tgatcttgga agctgttgcc     120
aaaggccaag aaattttcgg cattgagcag ccaaaacatg cagcacaact ctggtttcac     180
tccctgtgca ccgcaattgt cggccccgcc gtcaccgcca tggtggaatt cgatgtcatc     240
cccagcctcg acatacgtcg aggtcagctg cataacatcg acggttactg gttcggcttc     300
aggccggagg agatgcttgt cgacgcctcc ctccacctgt cgggcaccca attcggcgag     360
agtatccgcg tggtgattga tgcattatgc gctgccacgg atctgcgacc ggcacccctg     420
tgggcggttg cctcagatgc gttgggaatc gcagctagcg gcgcaggtgt cgaggccttt     480
gaagaagaac atgcccgcga ggtggcggaa gccctcattg aaggaatgaa tagtgtgaac     540
tcagttccat cgccgcggtt taacgacgac gattatttca ttcgagctgg atgctgcatg     600
attttccact caccacgagc tgattttgc acgtcgtgcc cacagaagag gtga            654

<210> SEQ ID NO 3
<211> LENGTH: 39
<212> TYPE: DNA
<213> ORGANISM: Artificial Sequence
<220> FEATURE:
<223> OTHER INFORMATION: synthetic

<400> SEQUENCE: 3
atgacatgat tacgaattca cactcctctg gctaggtag                             39

<210> SEQ ID NO 4
<211> LENGTH: 21
<212> TYPE: DNA
<213> ORGANISM: Artificial Sequence
<220> FEATURE:
<223> OTHER INFORMATION: synthetic

<400> SEQUENCE: 4
atgatgtcgg tggtgccgtc t                                                21

```
<210> SEQ ID NO 5
<211> LENGTH: 38
<212> TYPE: DNA
<213> ORGANISM: Artificial Sequence
<220> FEATURE:
<223> OTHER INFORMATION: synthetic

<400> SEQUENCE: 5
acggcaccac cgacatcatc ttcacctgcc ctcgttcc                          38

<210> SEQ ID NO 6
<211> LENGTH: 39
<212> TYPE: DNA
<213> ORGANISM: Artificial Sequence
<220> FEATURE:
<223> OTHER INFORMATION: synthetic

<400> SEQUENCE: 6
ggtcgactct agaggatcca cgcaggtgcc tgagacctt                         39

<210> SEQ ID NO 7
<211> LENGTH: 39
<212> TYPE: DNA
<213> ORGANISM: Artificial Sequence
<220> FEATURE:
<223> OTHER INFORMATION: synthetic

<400> SEQUENCE: 7
atgacatgat tacgaattca tctctgtgca ctcatctac                         39

<210> SEQ ID NO 8
<211> LENGTH: 20
<212> TYPE: DNA
<213> ORGANISM: Artificial Sequence
<220> FEATURE:
<223> OTHER INFORMATION: synthetic

<400> SEQUENCE: 8
tgctaattcc tcgagcgtga                                              20

<210> SEQ ID NO 9
<211> LENGTH: 39
<212> TYPE: DNA
<213> ORGANISM: Artificial Sequence
<220> FEATURE:
<223> OTHER INFORMATION: synthetic

<400> SEQUENCE: 9
cacgctcgag gaattagcac gagctggatg ctgcatgat                         39

<210> SEQ ID NO 10
<211> LENGTH: 39
<212> TYPE: DNA
<213> ORGANISM: Artificial Sequence
<220> FEATURE:
<223> OTHER INFORMATION: synthetic

<400> SEQUENCE: 10
agttattggt gcccttcgat tccaaaagtg cagcctaga                         39

<210> SEQ ID NO 11
<211> LENGTH: 24
<212> TYPE: DNA
<213> ORGANISM: Artificial Sequence
<220> FEATURE:
<223> OTHER INFORMATION: synthetic
```

```
<400> SEQUENCE: 11
ttcatgctaa ttcctcgagc gtga                                          24

<210> SEQ ID NO 12
<211> LENGTH: 24
<212> TYPE: DNA
<213> ORGANISM: Artificial Sequence
<220> FEATURE:
<223> OTHER INFORMATION: synthetic

<400> SEQUENCE: 12
aaactcacgc tcgaggaatt agca                                          24

<210> SEQ ID NO 13
<211> LENGTH: 39
<212> TYPE: DNA
<213> ORGANISM: Artificial Sequence
<220> FEATURE:
<223> OTHER INFORMATION: synthetic

<400> SEQUENCE: 13
acaggtacag tgtaattcag ttttagagct agaaatagc                          39

<210> SEQ ID NO 14
<211> LENGTH: 20
<212> TYPE: DNA
<213> ORGANISM: Artificial Sequence
<220> FEATURE:
<223> OTHER INFORMATION: synthetic

<400> SEQUENCE: 14
tcagtcacct cctagctgac                                               20

<210> SEQ ID NO 15
<211> LENGTH: 20
<212> TYPE: DNA
<213> ORGANISM: Artificial Sequence
<220> FEATURE:
<223> OTHER INFORMATION: synthetic

<400> SEQUENCE: 15
gtcagctagg aggtgactga                                               20

<210> SEQ ID NO 16
<211> LENGTH: 20
<212> TYPE: DNA
<213> ORGANISM: Artificial Sequence
<220> FEATURE:
<223> OTHER INFORMATION: synthetic

<400> SEQUENCE: 16
tgaattacac tgtacctgtt                                               20
```